United States Patent
Omiya et al.

(10) Patent No.: US 12,193,818 B2
(45) Date of Patent: Jan. 14, 2025

(54) INFORMATION PROCESSING APPARATUS, METHOD, AND PROGRAM

(71) Applicants: PST INC., Kanagawa (JP); THE UNIVERSITY OF TOKYO, Tokyo (JP)

(72) Inventors: Yasuhiro Omiya, Kanagawa (JP); Shuji Shinohara, Tokyo (JP)

(73) Assignees: PST INC., Kanagawa (JP); THE UNIVERSITY OF TOKYO, Tokyo (JP)

( * ) Notice: Subject to any disclaimer, the term of this patent is extended or adjusted under 35 U.S.C. 154(b) by 305 days.

(21) Appl. No.: 17/919,608

(22) PCT Filed: Mar. 16, 2021

(86) PCT No.: PCT/JP2021/010502
§ 371 (c)(1),
(2) Date: Oct. 18, 2022

(87) PCT Pub. No.: WO2021/220646
PCT Pub. Date: Nov. 4, 2021

(65) Prior Publication Data
US 2023/0148264 A1    May 11, 2023

(30) Foreign Application Priority Data
Apr. 28, 2020 (JP) ................. 2020-078995

(51) Int. Cl.
*G10L 25/63* (2013.01)
*A61B 5/00* (2006.01)
(Continued)

(52) U.S. Cl.
CPC ............ *A61B 5/165* (2013.01); *A61B 5/4803* (2013.01); *G10L 25/63* (2013.01); *G10L 25/66* (2013.01); *A61B 5/4842* (2013.01)

(58) Field of Classification Search
CPC ..... A61B 5/165; A61B 5/4803; A61B 5/4842; G10L 25/63
(Continued)

(56) References Cited

U.S. PATENT DOCUMENTS

| | | | |
|---|---|---|---|
| 7,678,047 B2 * | 3/2010 | Shiomi | A61B 5/4064 600/587 |
| 11,918,372 B2 * | 3/2024 | Sumi | G10L 25/66 |
| 2019/0281398 A1 * | 9/2019 | Yamaguchi | G10K 11/17835 |

FOREIGN PATENT DOCUMENTS

| | | | |
|---|---|---|---|
| JP | 3351746 B2 * | 12/2002 | H04B 1/665 |
| JP | 2016-4507 A | 1/2016 | |

(Continued)

OTHER PUBLICATIONS

O. T. -C. Chen, Y. H. Tsai, C. W. Su, P. C. Kuo and W. C. Lai, "Voice-activity home care system," 2016 IEEE-EMBS International Conference on Biomedical and Health Informatics (BHI), Las Vegas, NV, USA, 2016, pp. 110-113, doi: 10.1109/BHI.2016.7455847. keywords: {Noise reduction; Speaker recognition; (Year: 2016).*

(Continued)

*Primary Examiner* — Bharatkumar S Shah
(74) *Attorney, Agent, or Firm* — GREENBLUM & BERNSTEIN, P.L.C.

(57) ABSTRACT

An object of the present invention is to provide an information processing apparatus capable of more easily evaluating a depression state. The present invention is an information processing apparatus including: means for inputting voice data uttered by a subject; means for acquiring time-series data of sound pressure in the input voice data; and means for obtaining a Sound Pressure Change acceleration index that is an index based on a force toward a center and a force away from the center of the acquired time-series data of the sound pressure.

5 Claims, 17 Drawing Sheets

(51) Int. Cl.
*A61B 5/16* (2006.01)
*G10L 25/66* (2013.01)

(58) Field of Classification Search
USPC .......................................................... 704/270
See application file for complete search history.

(56) References Cited

FOREIGN PATENT DOCUMENTS

| JP | 2017-26823 | 2/2017 |
| WO | 2019/087758 | 5/2019 |
| WO | 2020/013296 A1 | 1/2020 |

OTHER PUBLICATIONS

Shinohara, S. et al., "Evaluation of emotional arousal level and depression severity using voice-derived sound pressure change acceleration", Science Reports, 11, 13615, Jun. 30, 2021, pp. 1-11.
International Search Report issued in International Bureau of WIPO Patent Application No. PCT/JP2021/010502, dated Jun. 1, 2021, along with an English translation thereof.
Apr. 29, 2024 Extended European Search Report in European Application No. 21796222.4.

\* cited by examiner

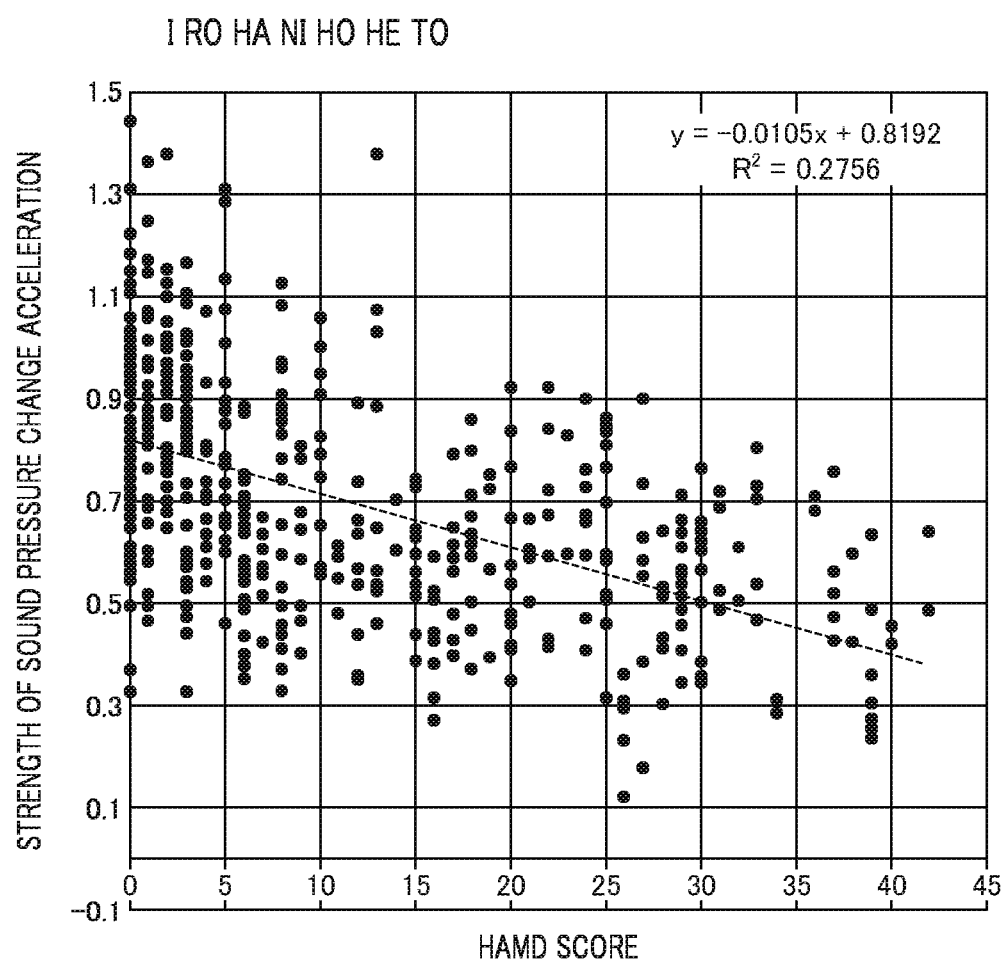

INFORMATION PROCESSING APPARATUS, METHOD, AND PROGRAM

TECHNICAL FIELD

The present invention relates to an information processing apparatus, a method, and a program, and more particularly, to measurement of a health condition of a subject.

BACKGROUND ART

Heretofore, the Hamilton Depression Rating Scale (hereinafter referred to as "HAMD") has been known as a scale for evaluating a depression state of a subject. This HAMD is not a self-assessment scale of the subject, but is a scale in which scoring is performed in a form in which a doctor or the like in charge of an examination conducts an interview and the depression state of the subject is evaluated according to a result thereof.

In addition, Patent Literature 1 discloses that a medical interview result is input to a health state presentation device to evaluate the medical interview result.

CITATION LIST

Patent Literature

Patent Literature 1: JP 2016-4507 A

SUMMARY OF INVENTION

Technical Problem

However, conventionally, it is necessary for a doctor or the like in charge of an examination to perform scoring in a form of an interview with a subject for about 30 minutes, which may be a burden to both the subject and the examiner. Provision of an index capable of more easily evaluating a depression state of the subject has been desired.

The present invention has been made in view of such a situation, and an object thereof is to provide an information processing apparatus capable of more easily evaluating presence or absence of depression or severity of the depression.

Solution to Problem

In order to solve the above problem, the present invention is an information processing apparatus including: means for inputting voice data uttered by a subject; means for acquiring time-series data of sound pressure in the input voice data; and means for obtaining a Sound Pressure Change acceleration index that is an index based on a force toward a center and a force away from the center of the acquired time-series data of the sound pressure.

Advantageous Effects of Invention

According to the present invention, it is possible to provide an information processing apparatus capable of more easily evaluating presence or absence of depression or severity of the depression.

BRIEF DESCRIPTION OF DRAWINGS

FIG. 5A is a graph showing a correlation between the strength of the Sound Pressure Change acceleration and the HAMD score by making a phrase uttered by a subject different in order to obtain the strength of the Sound Pressure Change acceleration.

DESCRIPTION OF EMBODIMENTS

Hereinafter, a mode for carrying out the present invention will be described in detail with reference to the drawings.

First Embodiment

Figure 1:
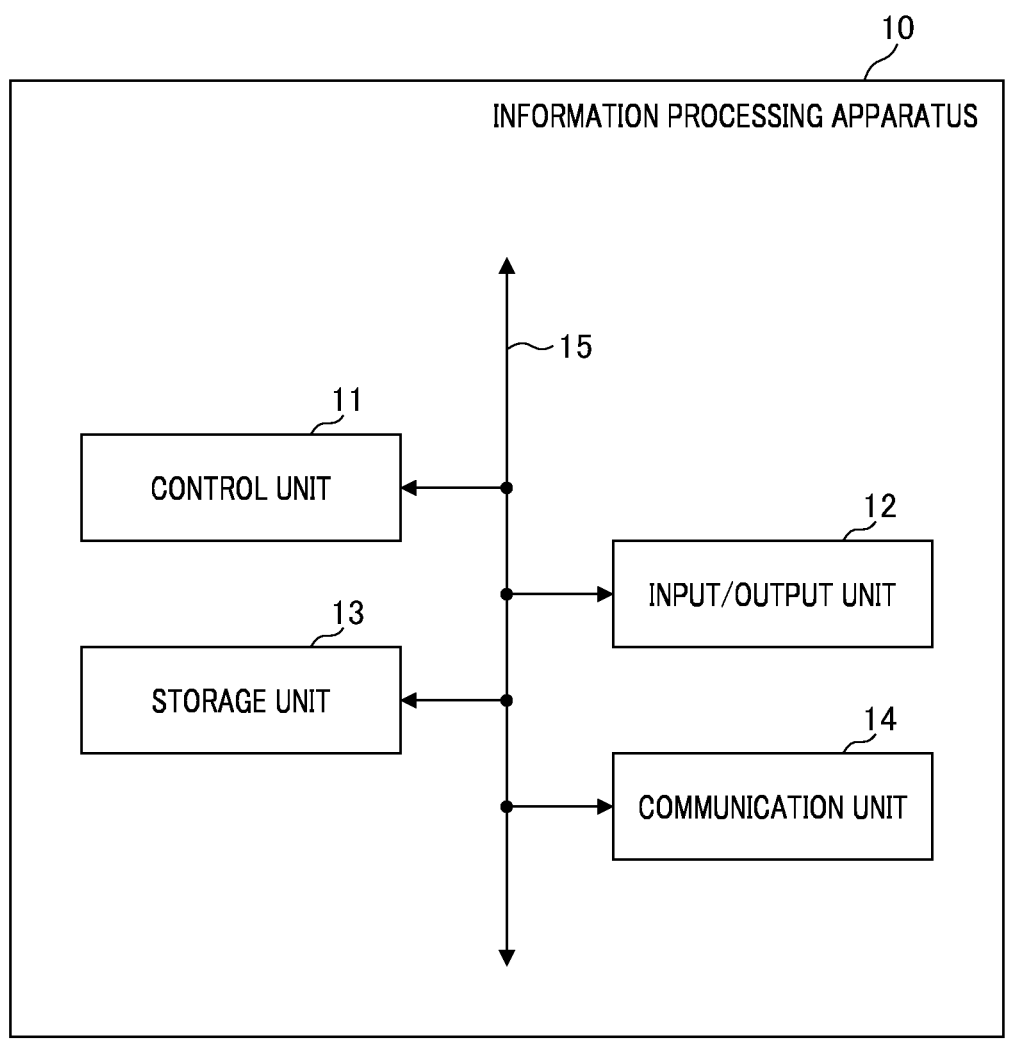
FIG. 1 is a block diagram illustrating an example of a configuration of an information processing apparatus according to a first embodiment of the present invention.

FIG. 1 is a block diagram illustrating an example of a configuration of an information processing apparatus according to a first embodiment of the present invention. An information processing apparatus 10 includes a control unit 11 that controls entire operation, an input/output unit 12 that performs various types of input/output, a storage unit 13 that stores various types of data, programs, and the like, a communication unit 14 that performs communication with the outside, and an internal bus 15 that connects the blocks so that the blocks can communicate with each other.

The information processing apparatus 10 is, for example, a computer, and may be a device that can be carried by a subject, such as a smartphone, a PDA, a tablet, or a laptop computer, or may be a computer that is fixed at an installation position without being carried by the subject. PDA is an abbreviation for Personal Digital Assistant.

The control unit 11 is, for example, a device called a CPU, an MCU, or an MPU, and for example, a program stored in the storage unit 13 is executed. CPU is an abbreviation for Central Processing Unit. MCU is an abbreviation for Micro Controller Unit. MPU is an abbreviation for Micro Processor Unit.

The input/output unit 12 is a device that performs input/output with respect to a subject who operates the information processing apparatus 10. The input/output unit 12 inputs and outputs information and signals by a display, a keyboard, a mouse, a button, a touch panel, a printer, a microphone, a speaker, and the like. In the present embodiment, the input/output unit 12 at least functions as a microphone, and inputs voice data by this microphone. Furthermore, in the present embodiment, the input/output unit 12 at least serves as a display, and displays a Sound Pressure Change acceleration index and a depression state to be described later on this display.

The storage unit 13 is, for example, a device such as a ROM, a RAM, an HDD, or a flash memory, and stores programs executed by the control unit 11 and various data. ROM is an abbreviation for Read Only Memory. RAM is an abbreviation for Random Access Memory. HDD is an abbreviation for Hard Disk Drive.

The communication unit 16 communicates with the outside. Communication by the communication unit 16 may be wired communication or wireless communication. The communication by the communication unit 16 may use any communication scheme. The control unit 11 can transmit and receive various data such as voice data by the communication unit 16. The control unit 11 may transmit a Sound Pressure Change acceleration index, presence or absence of depression, or severity of depression to be described later to an external device by the communication unit 16.

Figure 2:
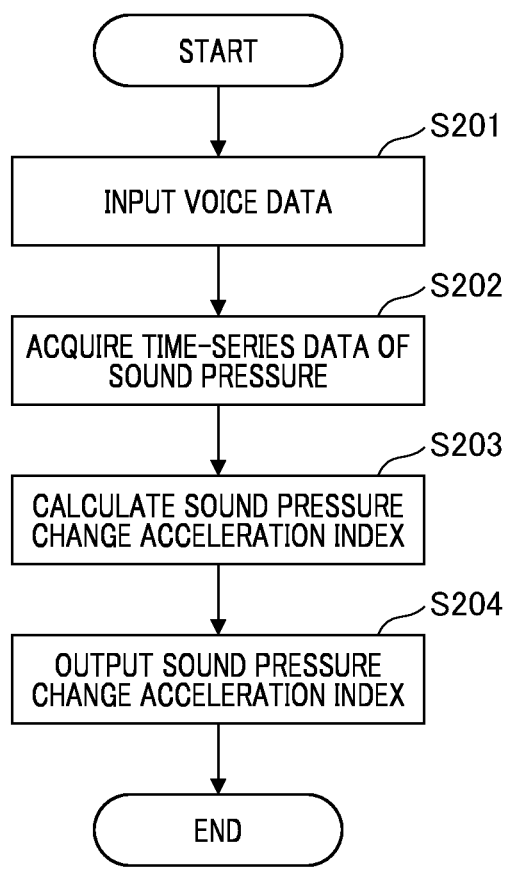
FIG. 2 is a flowchart illustrating an example of processing executed by an information processing apparatus 10.

FIG. 2 is a flowchart illustrating an example of processing executed by the information processing apparatus 10. In the present embodiment, as will be described in detail later, the Sound Pressure Change acceleration index (strength of a Sound Pressure Change acceleration) is obtained from an utterance of a subject. Since this Sound Pressure Change acceleration index has a correlation with a HAMD score as described later, it is possible to perform a screening test as an alternative in an environment where the HAMD cannot be performed only by asking the subject to make a simple utterance.

First, the control unit 11 inputs voice data of the subject by the input/output unit 12 (for example, a microphone) (step S201). At this time, the subject makes an utterance toward the microphone. The Sound Pressure Change acceleration index used in the present embodiment has little phrase dependency as described later. Therefore, accurate measurement can be performed even if the subject does not necessarily speak the same phrase and the number of utterances is small. Note that the voice data input in step S201 may be voice data recorded in advance. Subsequently, the control unit 11 acquires time-series data of sound pressure from the voice data input in step S201 (step S202). Subsequently, the control unit 11 calculates a Sound Pressure Change acceleration index from the time-series data of the sound pressure acquired in step S202 (step S203). Subsequently, the control unit 11 outputs the Sound Pressure Change acceleration index calculated in step S203 by the input/output unit 12 (for example, a display) (step S204). At this time, the Sound Pressure Change acceleration index itself may be output, the presence or absence of depression or the severity of depression of the subject corresponding to the Sound Pressure Change acceleration index may be output, or the HAMD score corresponding to the Sound Pressure Change acceleration index may be output.

Here, the time-series data of the sound pressure acquired in step S202 in FIG. 2 will be described.

Figure 3:
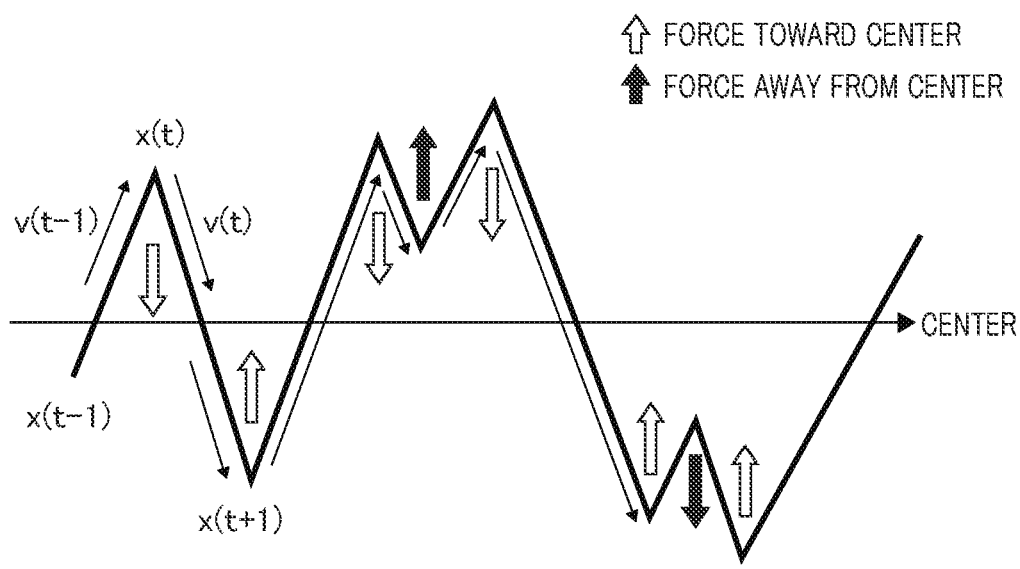
FIG. 3 is a diagram illustrating an example of time-series data of sound pressure.

FIG. 3 is a diagram illustrating an example of time-series data of sound pressure. In FIG. 3, the horizontal axis represents time, and the vertical axis represents sound pressure. In step S202, the sound pressure is obtained for each time from the voice data input in step S201. The example of FIG. 3 illustrates that the voice data input in step S201 has the sound pressure of $x(t-1)$ at time $t-1$, the sound pressure of $x(t)$ at time $t$, and the sound pressure of $x(t+1)$ at time $t+1$.

Next, the Sound Pressure Change acceleration index calculated in step S203 in FIG. 2 will be described.

First, for example, an intermediate value between the maximum value and the minimum value of the sound pressure is defined as the center. In FIG. 3, the sound pressure changes from $x(t-1)$ to $x(t)$ from time $t-1$, and the sound pressure increases. Subsequently, the sound pressure changes from $x(t)$ to $x(t+1)$ from time $t$ to time $t+1$, and the sound pressure decreases.

When looking at a period from time $t-1$ to time $t+1$, since the sound pressure at time $t$ is above the center and the sound pressures at the preceding and subsequent times are below the center, it is assumed that a force toward the center is generated at time $t$.

In a case where the sound pressure at a certain time is above the center and the sound pressure at either one of the preceding and subsequent times is below the center, it is assumed that a force toward the center is generated at that time.

In a case where the sound pressure at a certain time is below the center and the sound pressure at either one of the preceding and subsequent times is above the center, it is assumed that a force toward the center is generated at that time.

In a case where the sound pressures at a certain time and before or after the certain time are above the center, and in a case where the sound pressure at the certain time is stronger than the sound pressure before or after the certain time, it is assumed that a force toward the center is generated at that time.

In a case where the sound pressures at a certain time and before or after the certain time are above the center, and in a case where the sound pressure at the certain time is weaker than the sound pressure before or after the certain time, it is assumed that a force away from the center is generated at that time.

If X(t) is above the center, a downward force, ie negative F(t), represents a force towards the center. Similarly, if X(t) is above the center, an upward force, ie positive F(t), represents a force away from the center.

Conversely, if X(t) is below the center, then a downward force, ie negative F(t), represents a force away from the center. Similarly, if X(t) is below the center, an upward force, ie positive F(t), represents a force towards the center.

Formula 1 is an expression for obtaining F(t) indicating a force toward the center and a force away from the center at time t.

$$v(t) = x(t+1) - x(t)$$
$$v(t-1) = x(t) - x(t-1)$$
$$F(t) = \frac{v(t) - v(t-1)}{\min(|v(t)|, |v(t-1)|)}$$
[Formula 1]

The strength of the Sound Pressure Change acceleration, that is, the Sound Pressure Change acceleration index is, for example, a value obtained by dividing a value obtained by subtracting the sum of forces away from the center from the sum of forces toward the center of the time-series data of the sound pressure by the total of the number of forces toward the center and the number of forces away from the center.

The following processing (1), (2), and (3) is performed to calculate the Sound Pressure Change acceleration index.

(1) F(t) is obtained by Formula 1.
(2) When X(t) is above the center, a sign of F(t) is reversed.
(3) When F(t) is positive, it is defined as a force toward the center, and when F(t) is negative, it is defined as a force away from the center.

Figure 4:
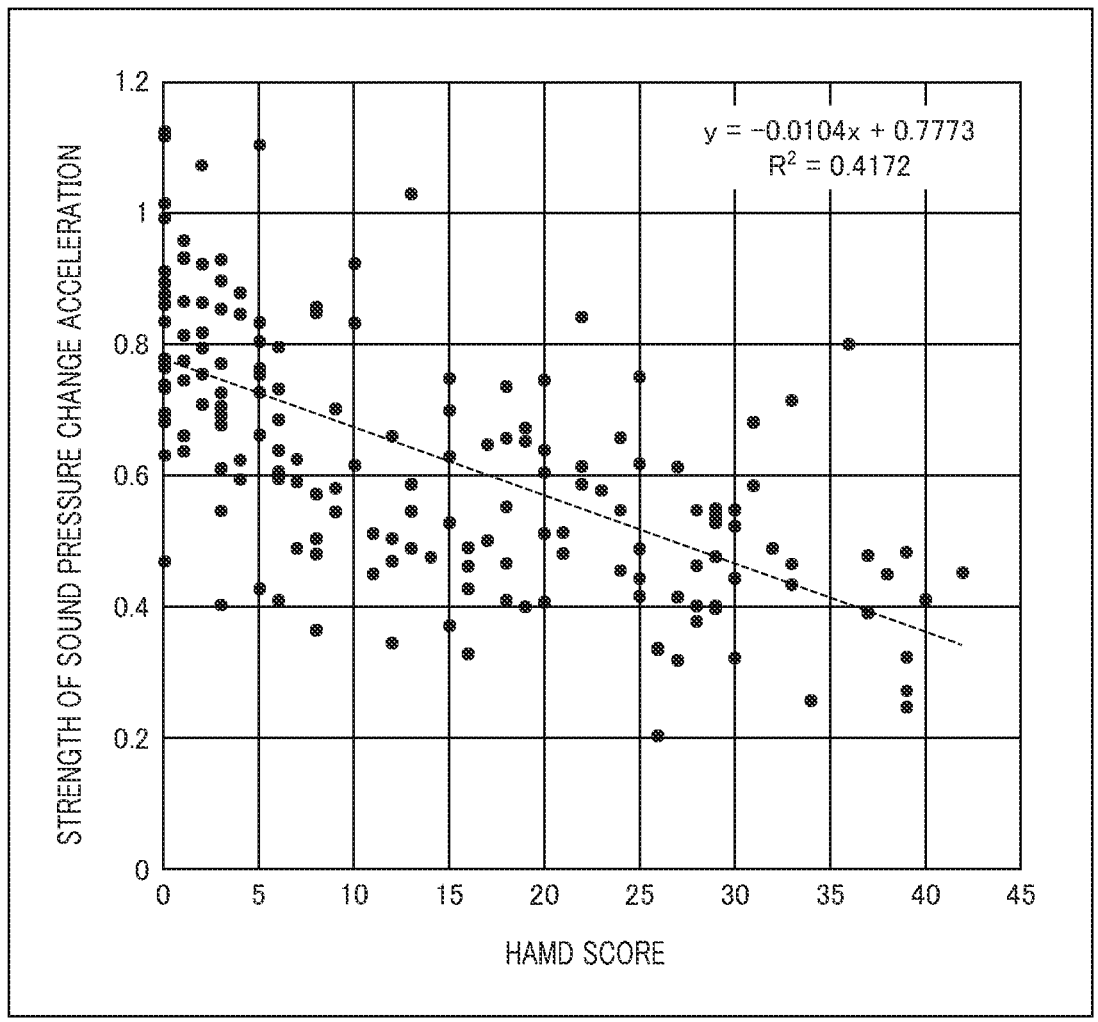
FIG. 4 is a graph in which data of a plurality of subjects is plotted, with strength of a Sound Pressure Change acceleration, that is, a Sound Pressure Change acceleration index, obtained by the information processing apparatus 10 of FIG. 1 for an utterance made by a subject on the vertical axis and a HAMD score of the subject on the horizontal axis.

FIG. 4 is a graph in which data of a plurality of subjects is plotted, with the strength of the Sound Pressure Change acceleration, that is, the Sound Pressure Change acceleration index obtained by the information processing apparatus 10 of FIG. 1 with respect to an utterance made by a subject on the vertical axis and a HAMD score of the subject on the horizontal axis. As shown in FIG. 4, a correlation is observed between the strength of the Sound Pressure Change acceleration and the HAMD score, and effectiveness of using the Sound Pressure Change acceleration index as a substitute in an environment where the HAMD score cannot be performed could be confirmed.

FIGS. 5A to 5J are graphs each illustrating a correlation between the strength of the Sound Pressure Change acceleration and the HAMD score by making a phrase uttered by a subject different to obtain the strength of the Sound Pressure Change acceleration as in FIG. 4.

The graph of FIG. 5A is a graph showing the correlation between the strength of the Sound Pressure Change acceleration and the HAMD score when uttering, "i ro ha ni ho he to".

Figure 5B:
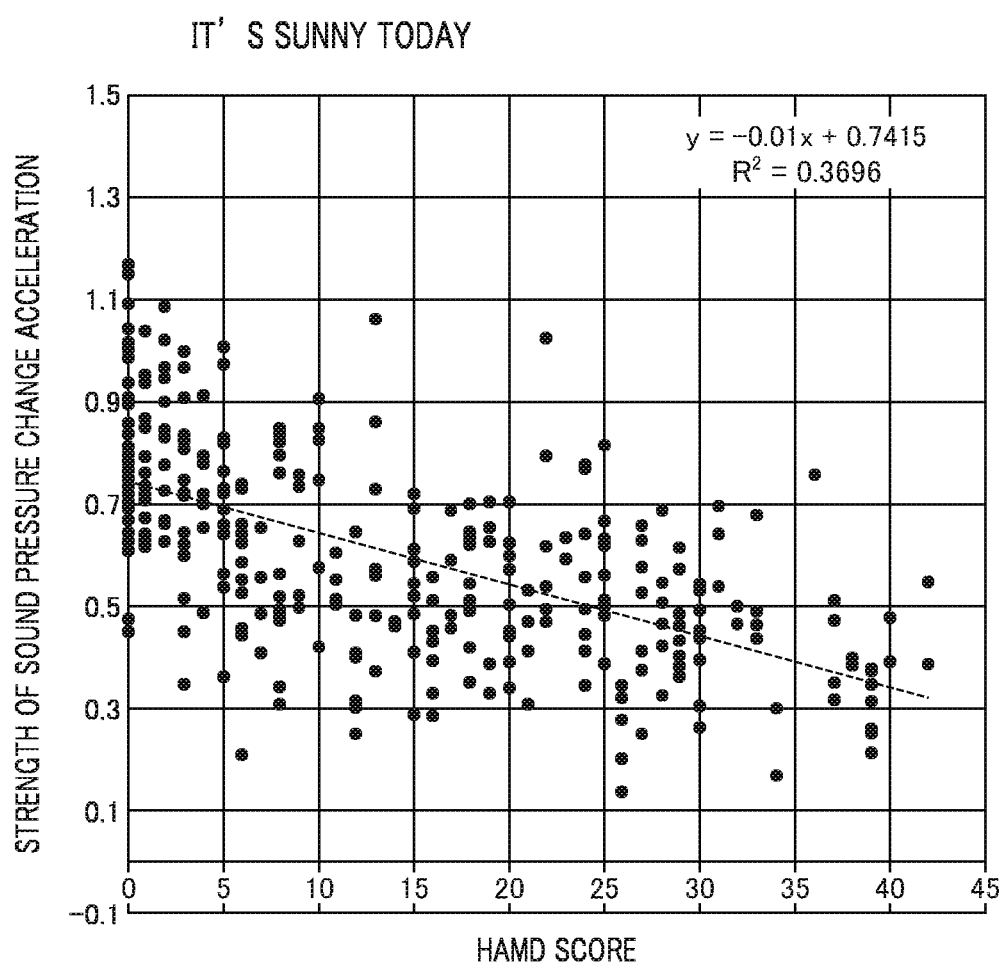
FIG. 5B is a graph showing the correlation between the strength of the Sound Pressure Change acceleration and the HAMD score by making a phrase uttered by the subject different in order to obtain the strength of the Sound Pressure Change acceleration.

The graph of FIG. 5B is a graph showing the correlation between the strength of the Sound Pressure Change acceleration and the HAMD score when uttering, "It's sunny today".

Figure 5C:
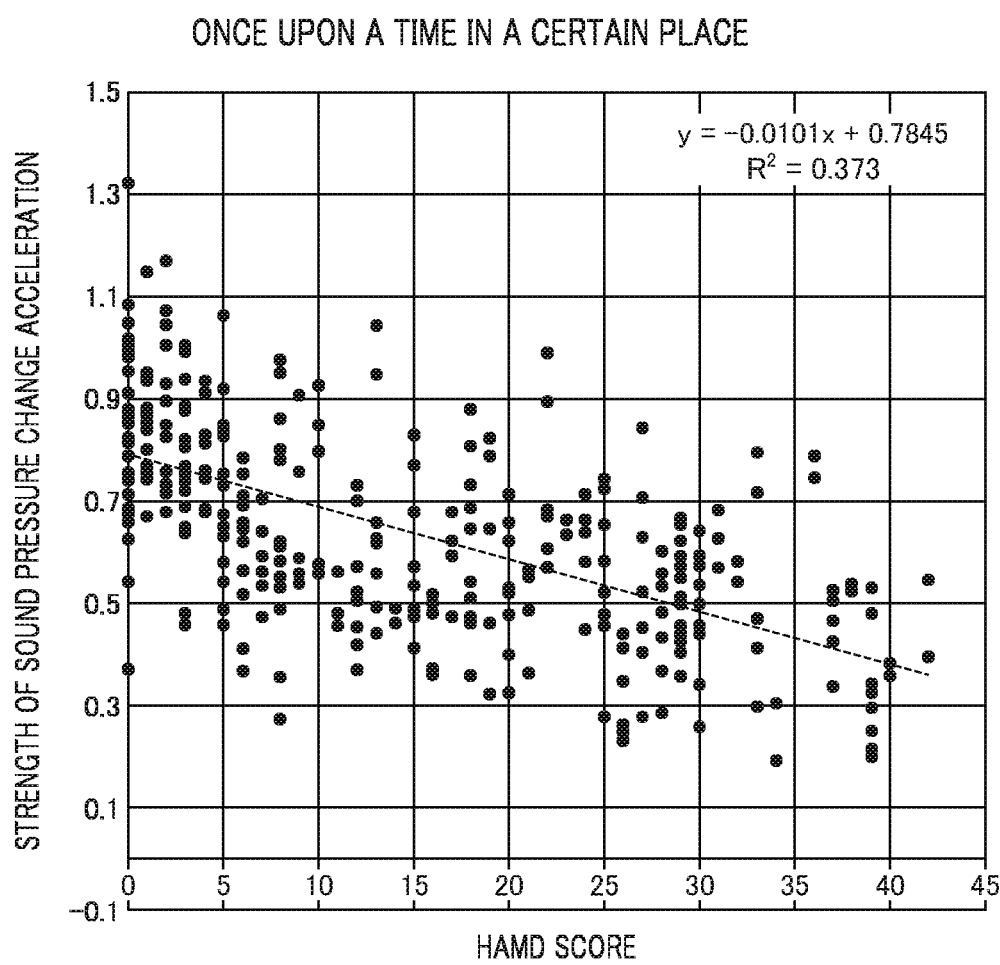
FIG. 5C is a graph showing the correlation between the strength of the Sound Pressure Change acceleration and the HAMD score by making a phrase uttered by the subject different in order to obtain the strength of the Sound Pressure Change acceleration.

The graph of FIG. 5C is a graph showing the correlation between the strength of the Sound Pressure Change acceleration and the HAMD score when uttering, "Once upon a time in a certain place".

Figure 5D:
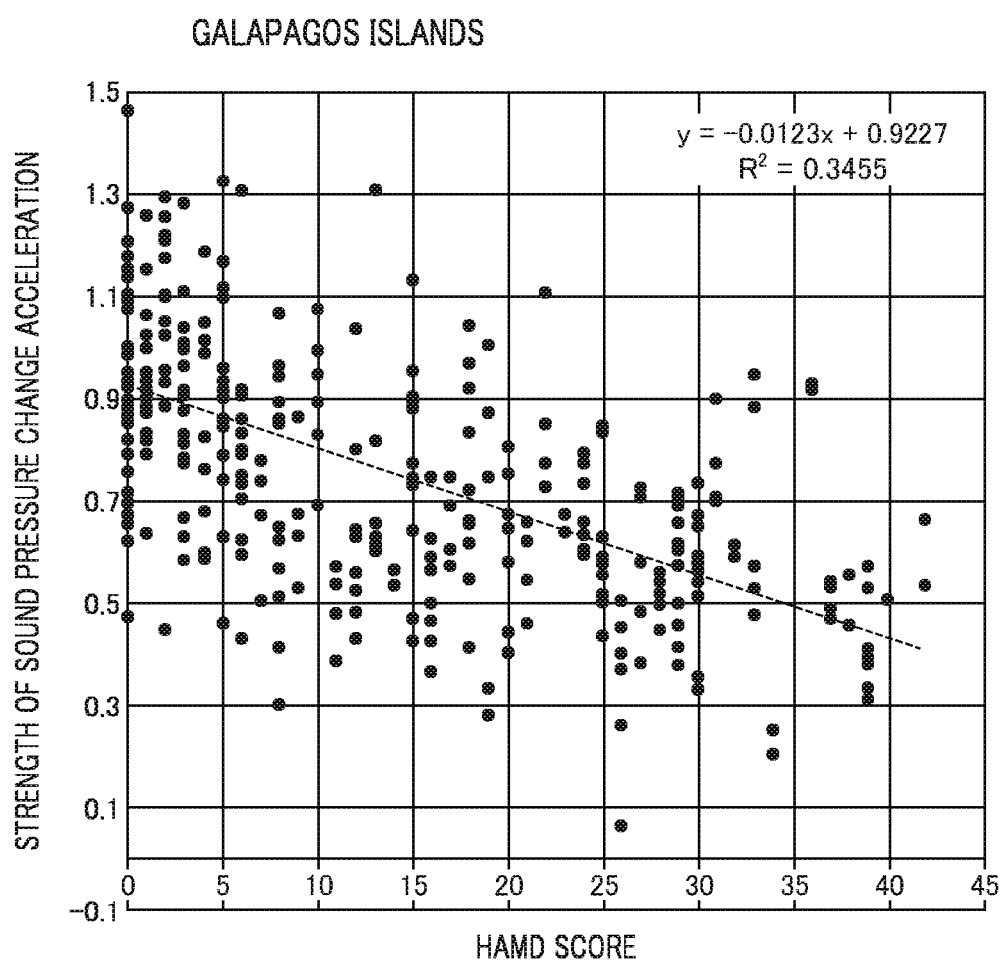
FIG. 5D is a graph showing the correlation between the strength of the Sound Pressure Change acceleration and the HAMD score by making a phrase uttered by the subject different in order to obtain the strength of the Sound Pressure Change acceleration.

The graph of FIG. 5D is a graph showing the correlation between the strength of the Sound Pressure Change acceleration and the HAMD score when uttering, "Galapagos islands".

Figure 5E:
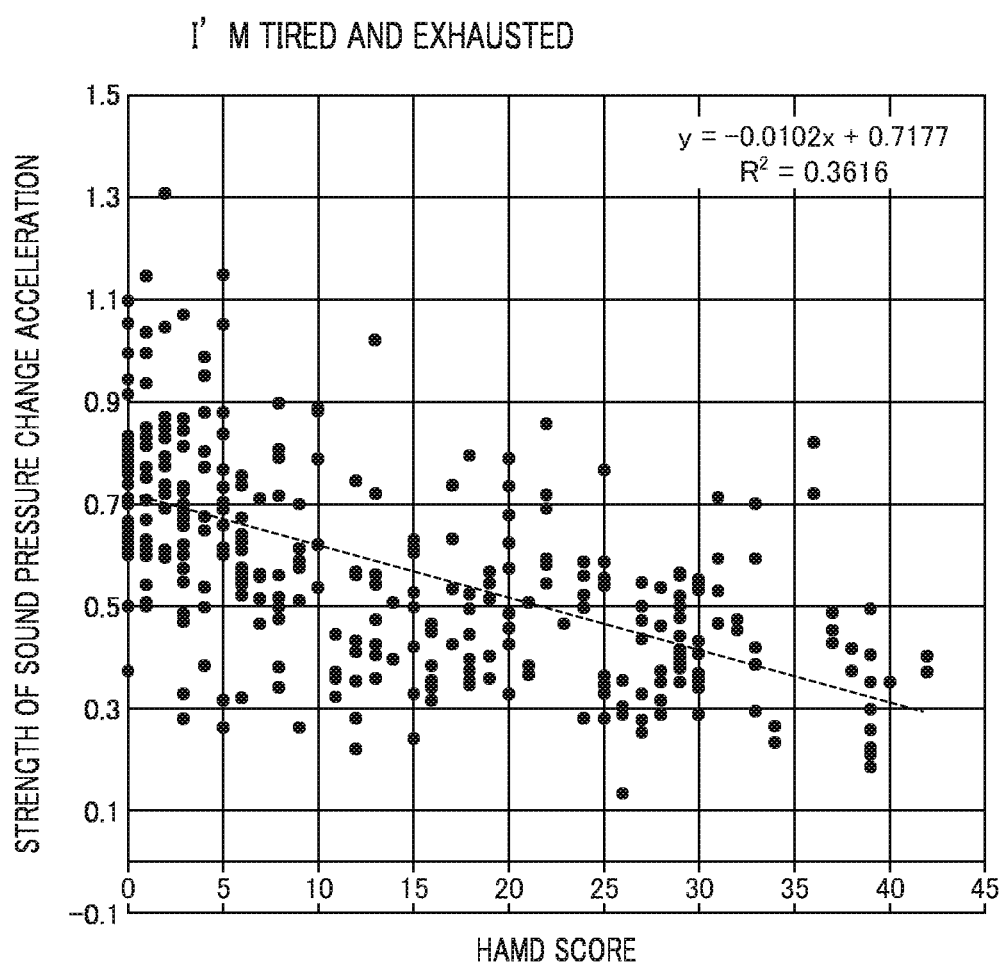
FIG. 5E is a graph showing the correlation between the strength of the Sound Pressure Change acceleration and the HAMD score by making a phrase uttered by the subject different in order to obtain the strength of the Sound Pressure Change acceleration.

The graph of FIG. 5E is a graph showing the correlation between the strength of the Sound Pressure Change acceleration and the HAMD score when uttering, "I'm tired and exhausted".

Figure 5F:
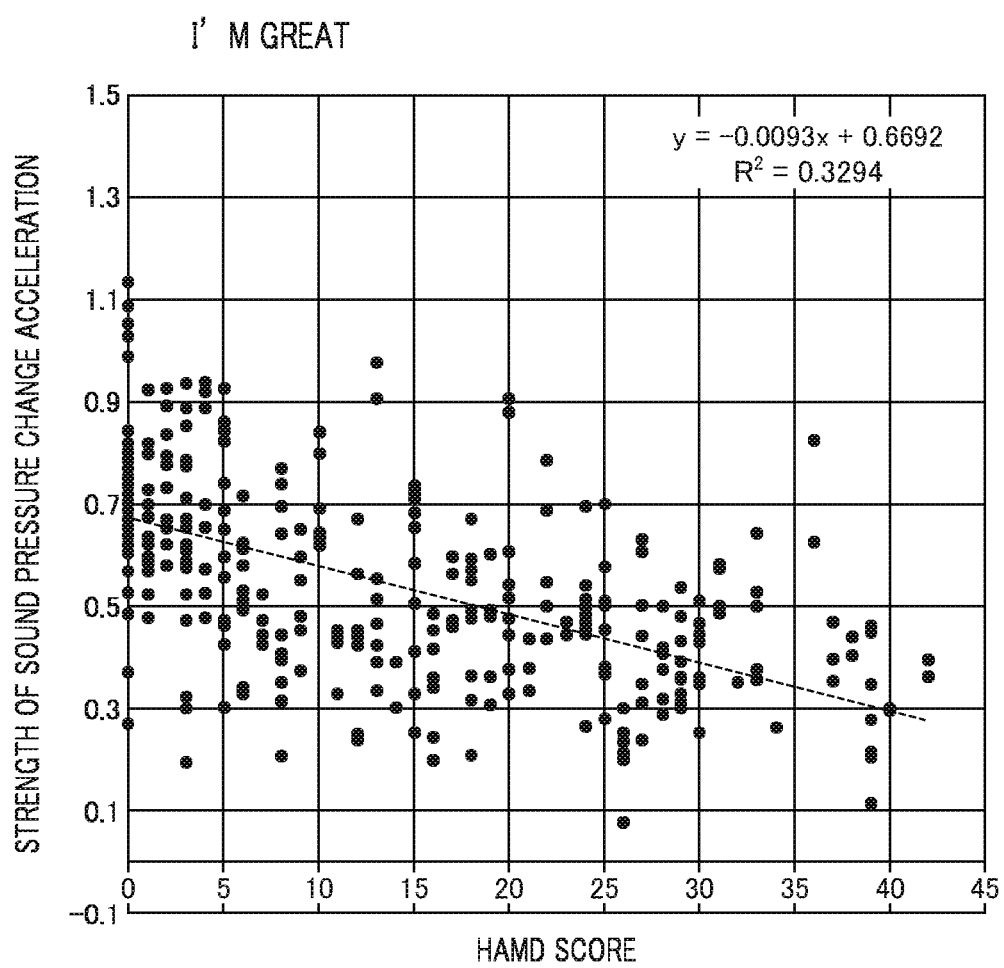
FIG. 5F is a graph showing the correlation between the strength of the Sound Pressure Change acceleration and the HAMD score by making a phrase uttered by the subject different in order to obtain the strength of the Sound Pressure Change acceleration.

The graph of FIG. 5F is a graph showing the correlation between the strength of the Sound Pressure Change acceleration and the HAMD score when uttering, "I'm great".

Figure 5G:
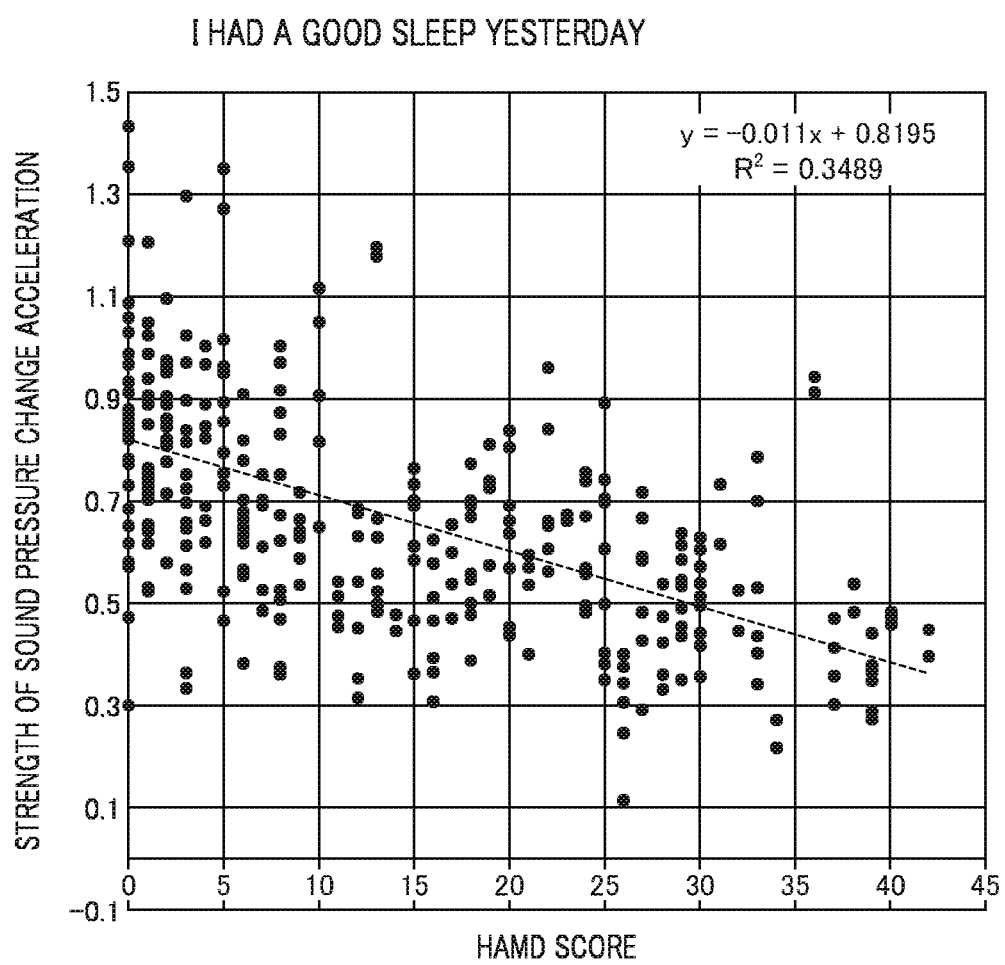
FIG. 5G is a graph showing the correlation between the strength of the Sound Pressure Change acceleration and the HAMD score by making a phrase uttered by the subject different in order to obtain the strength of the Sound Pressure Change acceleration.

The graph of FIG. 5G is a graph showing the correlation between the strength of the Sound Pressure Change acceleration and the HAMD score when uttering, "I had a good sleep yesterday".

Figure 5H:
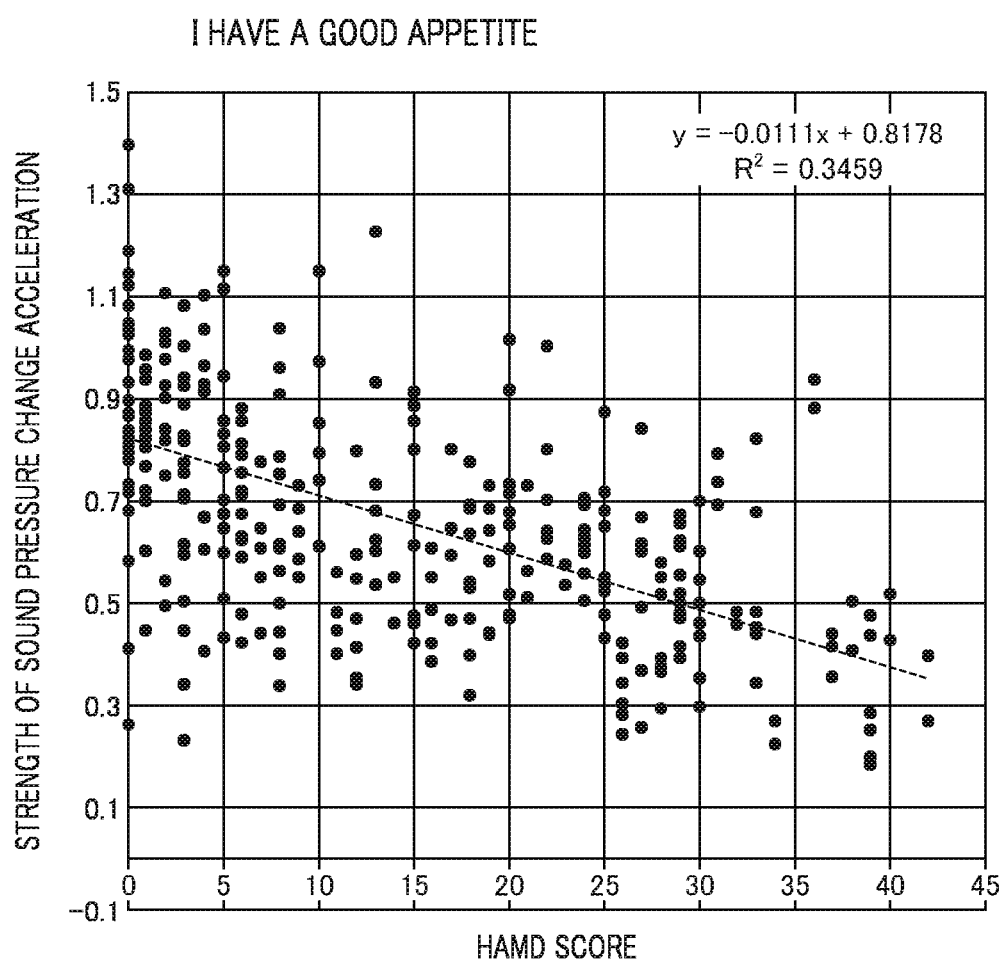
FIG. 5H is a graph showing the correlation between the strength of the Sound Pressure Change acceleration and the HAMD score by making a phrase uttered by the subject different in order to obtain the strength of the Sound Pressure Change acceleration.

The graph of FIG. 5H is a graph showing the correlation between the strength of the Sound Pressure Change acceleration and the HAMD score when uttering, "I have a good appetite".

Figure 5I:
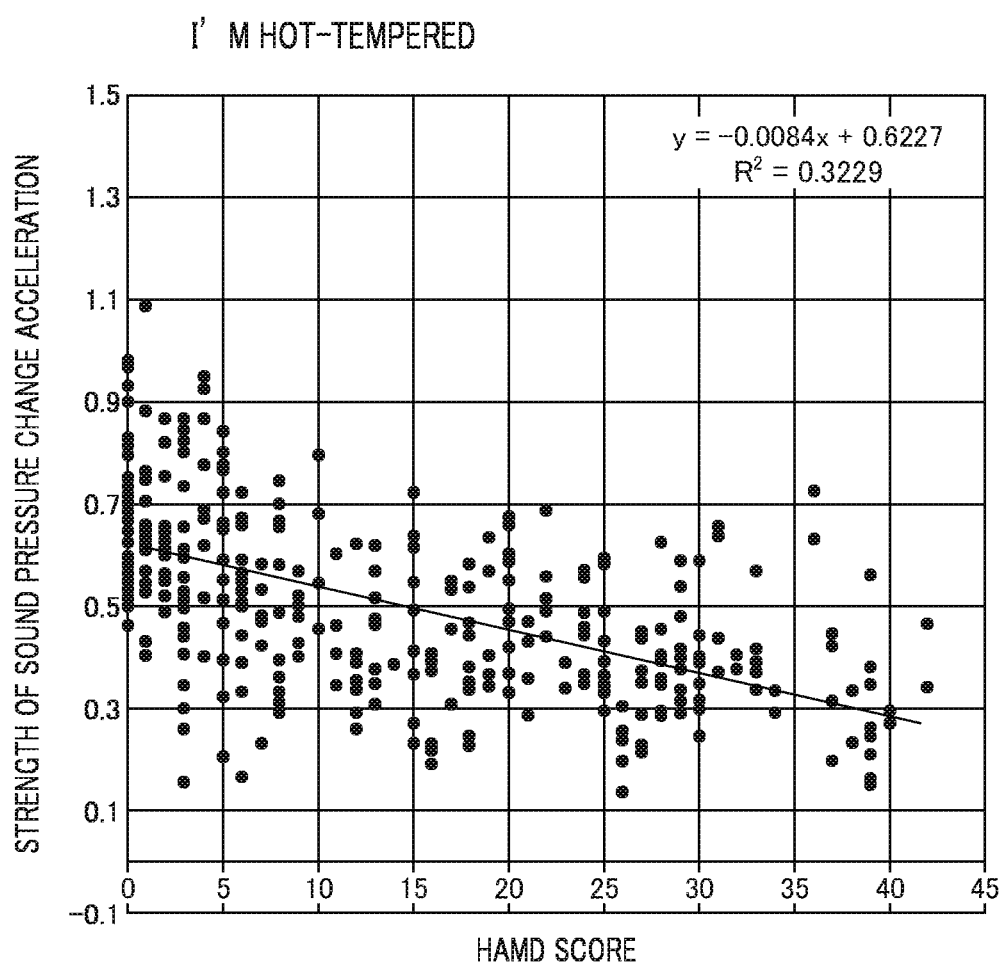
FIG. 5I is a graph showing the correlation between the strength of the Sound Pressure Change acceleration and the HAMD score by making a phrase uttered by the subject different in order to obtain the strength of the Sound Pressure Change acceleration.

The graph of FIG. 5I is a graph showing the correlation between the strength of the Sound Pressure Change acceleration and the HAMD score when uttering, "I'm hot-tempered".

Figure 5J:
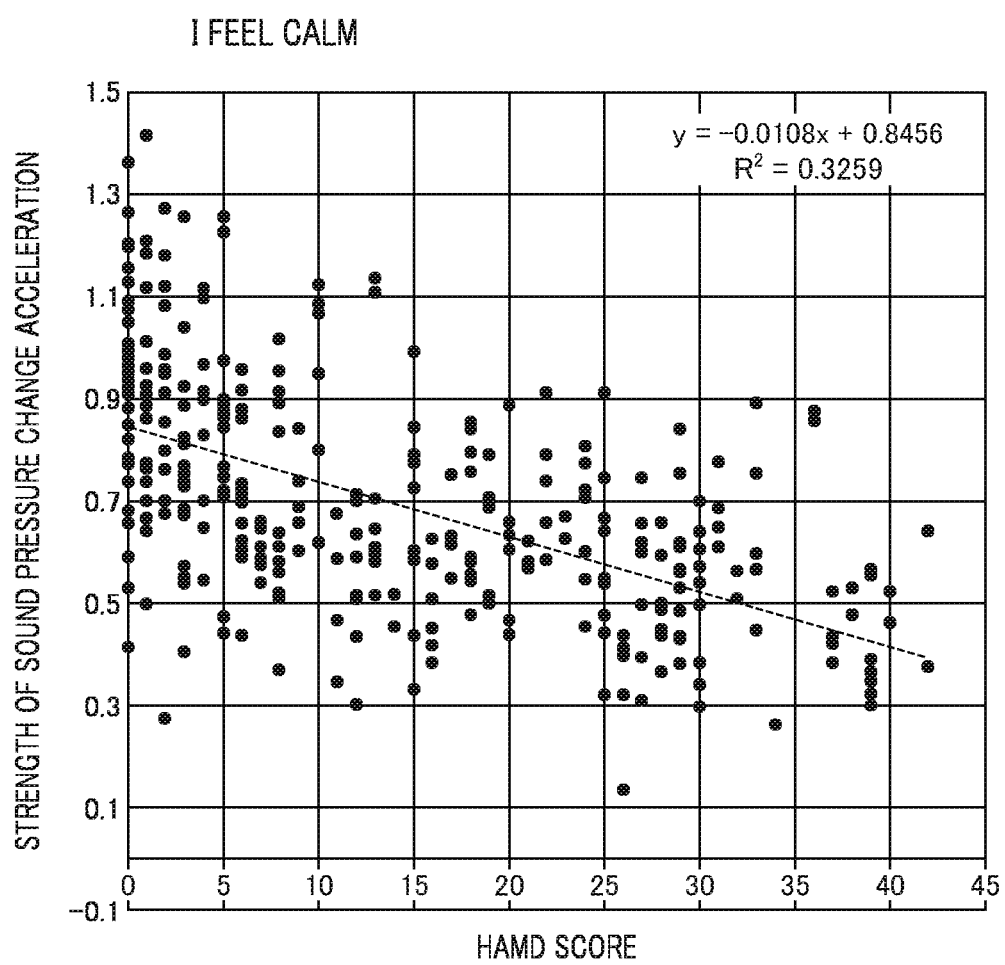
FIG. 5J is a graph showing the correlation between the strength of the Sound Pressure Change acceleration and the HAMD score by making a phrase uttered by the subject different in order to obtain the strength of the Sound Pressure Change acceleration.

The graph in FIG. 5J is a graph showing the correlation between the strength of the Sound Pressure Change acceleration and the HAMD score when uttering, "I feel calm".

Referring to the graphs in FIGS. 5A to 5J, it can be seen that the strength of the Sound Pressure Change acceleration and the HAMD score have a correlation without depending on the phrase.

FIG. 6 is a diagram illustrating an ROC curve of a result of screening healthy persons and depressed patients by the strength of the Sound Pressure Change acceleration obtained by the information processing apparatus 10 in FIG. 1.

Figure 6A:
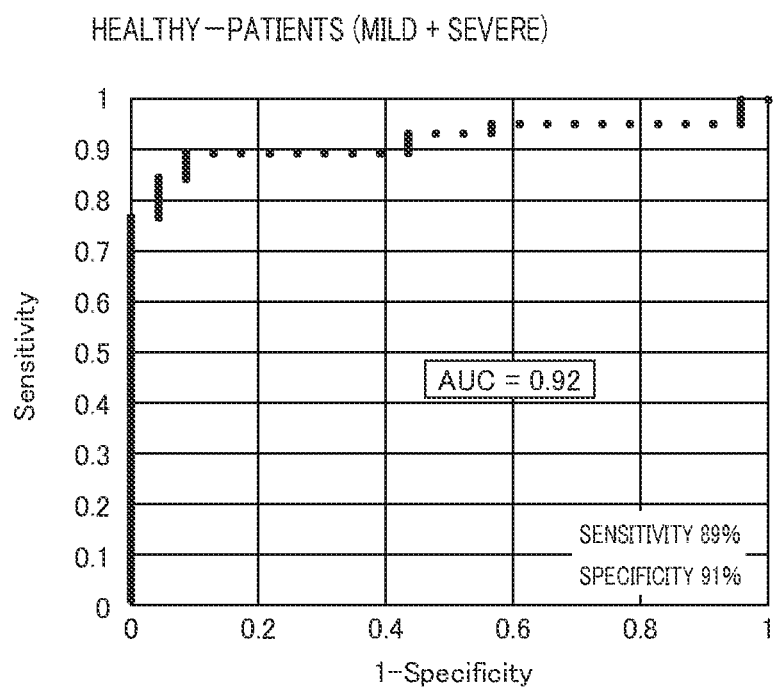
FIGS. 6A and 6B are graphs illustrating an ROC curve of a result of screening healthy persons and depressed patients by the strength of the Sound Pressure Change acceleration obtained by the information processing apparatus 10 in FIG. 1.

FIG. 6(A) illustrates a case of screening healthy persons and patients with mild and severe depression. As illustrated in FIG. 6(A), according to the information processing apparatus 10, an area under the curve (AUC) is 0.92. The AUC takes a value from 0.5 to 1, and the closer the value is to 1, the higher the discriminability is. Further, when sensitivity is 89%, the specificity is 91%. Thus, according to the information processing apparatus 10 of FIG. 1, screening with high discriminability can be performed.

Figure 6B:
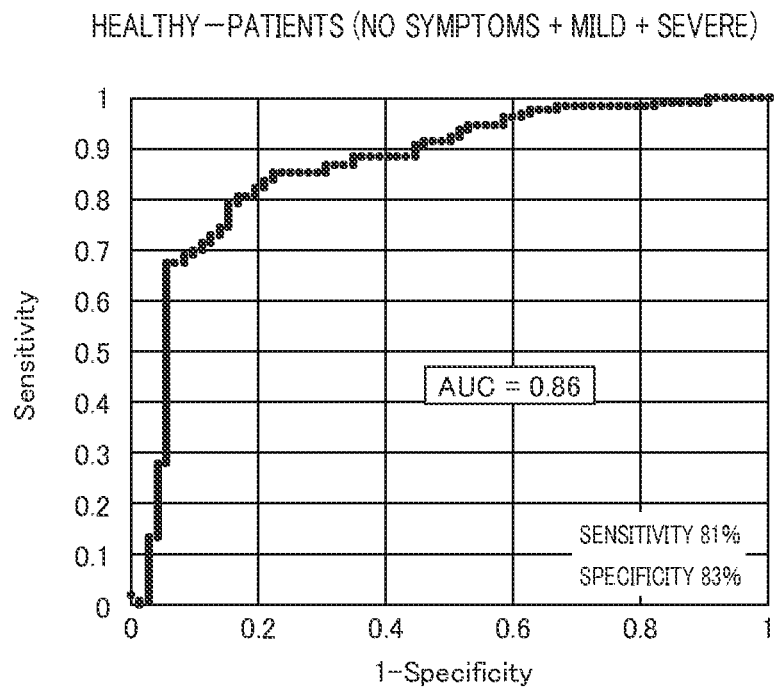

FIG. 6(B) shows a case of screening healthy persons and patients with No symptoms, mild, and severe depression. As illustrated in FIG. 6(B), the AUC is 0.86 according to the information processing apparatus 10. Further, when the sensitivity is 81%, the specificity is 83%. Thus, according to the information processing apparatus 10 of FIG. 1, screening with high discriminability can be performed.

FIG. 7 is a graph illustrating an ROC curve of a result of screening according to the severity of depression by the strength of the Sound Pressure Change acceleration obtained by the information processing apparatus 10 in FIG. 1.

Figure 7A:
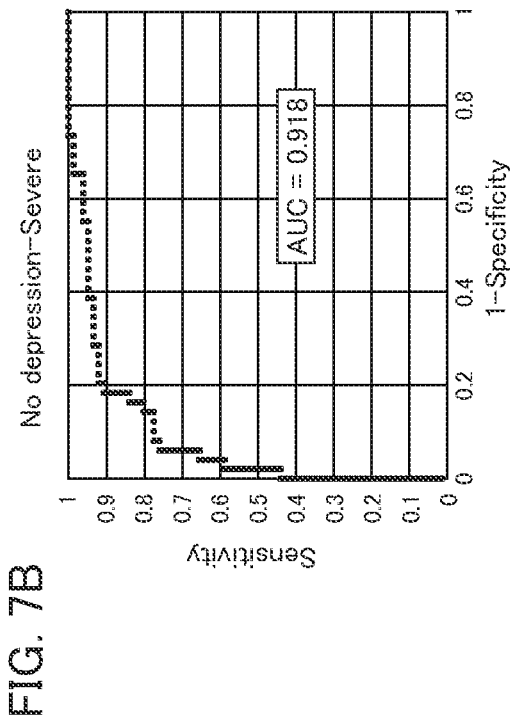
FIGS. 7A-7D are graphs showing an ROC curve of a result of screening according to severity of depression by the strength of the Sound Pressure Change acceleration obtained by the information processing apparatus 10 in FIG. 1.

FIG. 7(A) illustrates a case of screening patients with No symptoms depression (No depression) and patients with mild and severe depression (Depression). As illustrated in FIG. 7(A), the AUC is 0.814 according to the information processing apparatus 10. Thus, according to the information processing apparatus 10 of FIG. 1, screening with high discriminability can be performed.

Figure 7B:
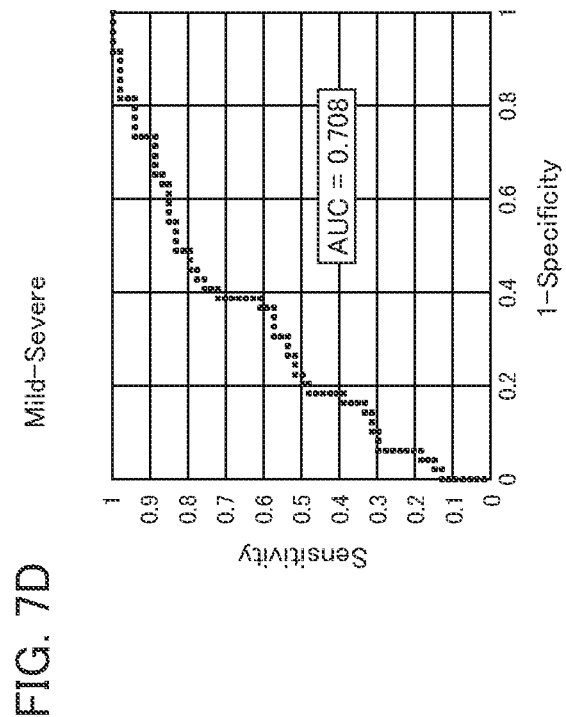

FIG. 7(B) illustrates a case of screening patients with No symptoms depression (No depression) and patients with severe depression (Severe). As illustrated in FIG. 7(B), the AUC is 0.918 according to the information processing apparatus 10. Thus, according to the information processing apparatus 10 of FIG. 1, screening with high discriminability can be performed.

Figure 7C:
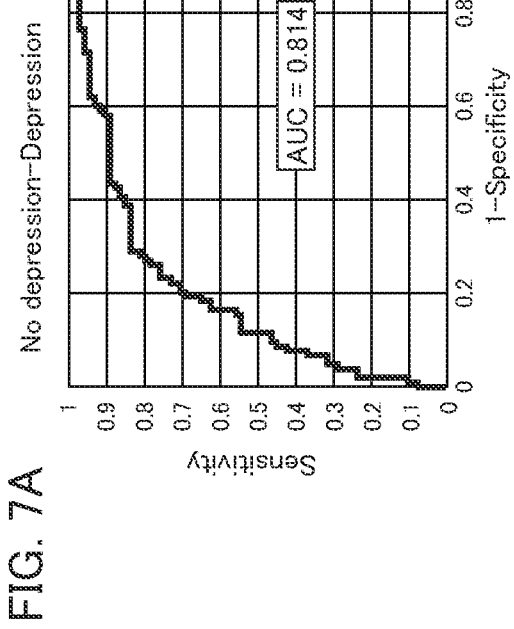

FIG. 7(C) illustrates a case of screening patients with No symptoms depression (No depression) and patients with mild depression (Mild). As illustrated in FIG. 7(C), the AUC is 0.795 according to the information processing apparatus 10. Thus, according to the information processing apparatus 10 of FIG. 1, screening with high discriminability can be performed.

Figure 7D:
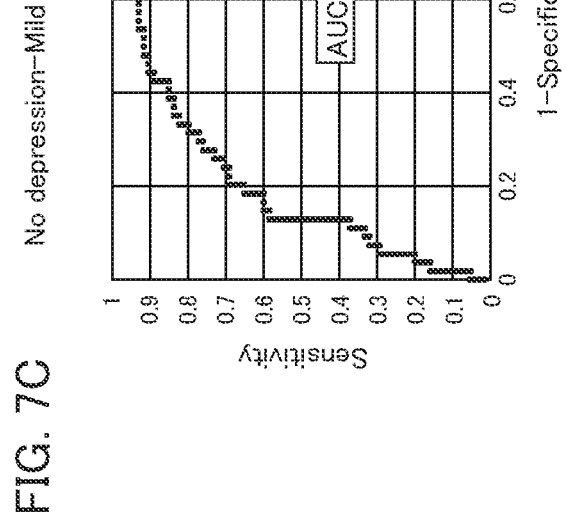

FIG. 7(D) shows a case of screening patients with mild depression (Mild) and patients with severe depression (Severe). As illustrated in FIG. 7(D), the AUC is 0.708 according to the information processing apparatus 10. Thus, according to the information processing apparatus 10 of FIG. 1, screening with high discriminability can be performed.

Figure 8:
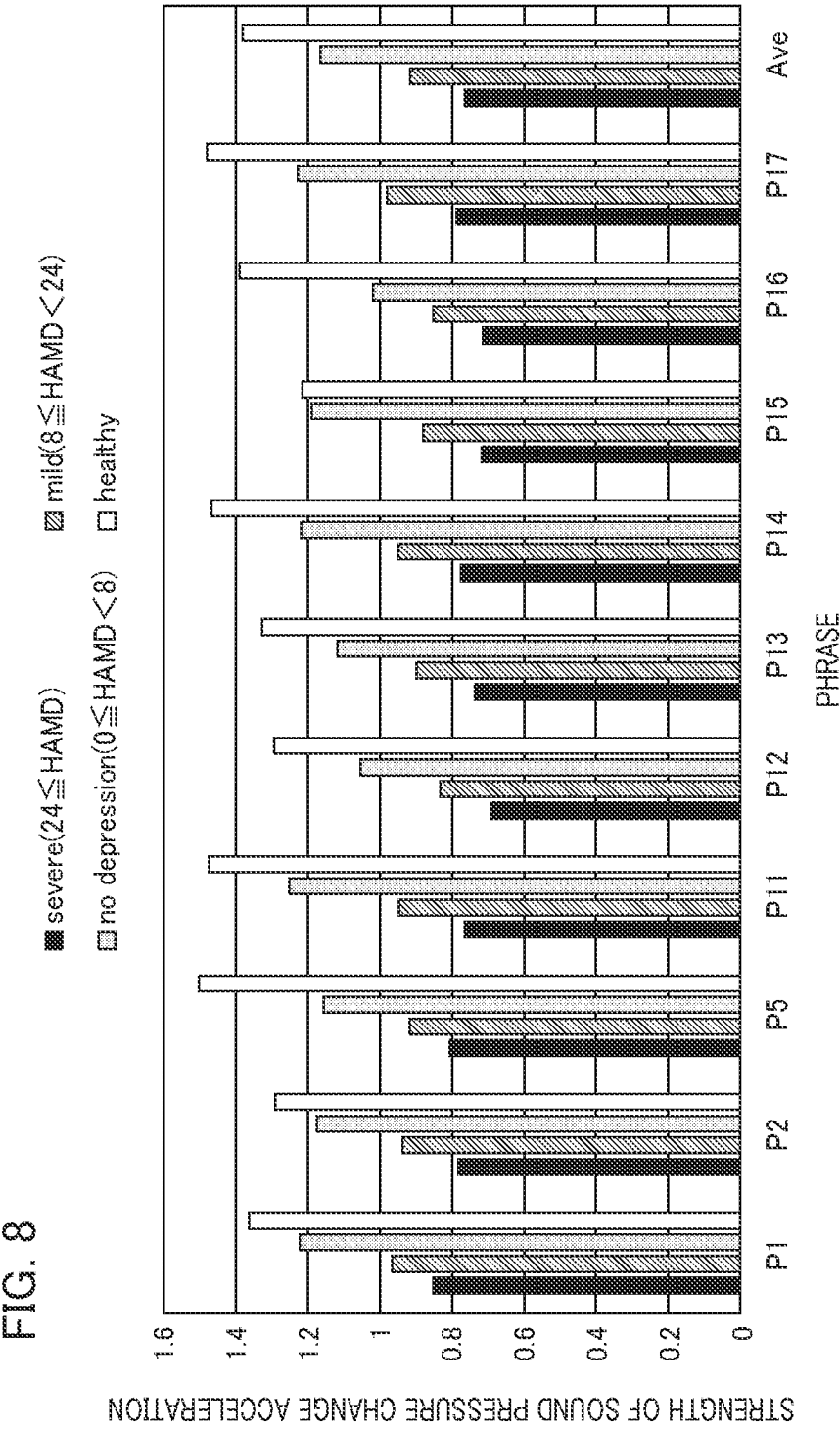
FIG. 8 is a graph showing, on the vertical axis, the strength of the Sound Pressure Change acceleration obtained by the information processing apparatus 10 of FIG. 1 for each of the plurality of utterances having different utterance contents by each of the healthy persons and the depressed patients.

FIG. 8 is a graph showing, on the vertical axis, the strength of the Sound Pressure Change acceleration Sound Pressure Change acceleration obtained by the information processing apparatus 10 of FIG. 1 for each of the plurality of utterances having different utterance contents by each of the healthy persons and the depressed patients.

In the graph of FIG. 8, each of the plurality of utterances having different utterance contents by each of the healthy persons and the depressed patients is arranged on the horizontal axis. In FIG. 8, phrases P1 to P12 are phrases having utterance contents different from each other. Ave is an average value of the phrases P1 to P12.

In FIG. 8, for each of the phrases P1 to P17 and the average value Ave, the strength of the Sound Pressure Change acceleration of patients with severe depression is indicated by the leftmost bar graph, the strength of the Sound Pressure Change acceleration of patients with mild depression is indicated by a second bar graph from the left, the strength of the Sound Pressure Change acceleration of patients with No symptoms depression is indicated by a third bar graph from the left, and the strength of the Sound Pressure Change acceleration of healthy persons is indicated by the rightmost bar graph.

Referring to FIG. 8, it can be seen that the strength of the Sound Pressure Change acceleration does not greatly change due to the difference in the utterance content uttered by the subject.

Although the preferred embodiment of the present invention has been described above, the present invention is not limited to the above-described embodiment. An object of the present invention is also achieved by supplying a storage medium storing a program code (computer program) for realizing the functions of the above-described embodiment to a system or an apparatus, and reading and executing the program code stored in the storage medium by a computer of the supplied system or apparatus. In this case, the program code itself read from the storage medium realizes the functions of the above-described embodiment, and the storage medium storing the program code constitutes the present invention. Furthermore, in the above-described embodiment, the computer executes the program to function as each processing unit, but a part or all of the processing may be configured by a dedicated electronic circuit (hardware). The present invention is not limited to the specific embodiment described above, and various modifications and changes can be made within the scope of the gist of the present invention described in the claims, including replacement of each configuration of each embodiment.

The present application claims priority based on JP 2020-78995 A filed on Apr. 28, 2020, the entire contents of which are incorporated herein by reference.

REFERENCE SIGNS LIST

10 Information processing apparatus
11 Control unit
12 Input/output unit
13 Storage unit
14 Communication unit
15 Internal bus

The invention claimed is:

1. An information processing apparatus comprising:
   an inputter for inputting voice data uttered by a subject;
   an acquirer for acquiring time-series data of sound pressure in the input voice data; and
   a calculator for calculating a Sound Pressure Change acceleration index that is an index based on a force toward a center and a force away from the center of the acquired time-series data of the sound pressure.

2. The information processing apparatus according to claim 1, wherein
   the Sound Pressure Change acceleration index is a value obtained by dividing a value obtained by subtracting a sum of forces away from the center from a sum of forces toward the center of the acquired time-series data of the sound pressure by a total of a number of forces toward the center and a number of forces away from the center.

3. The information processing apparatus according to claim 1, further comprising
   an outputter for outputting the obtained Sound Pressure Change acceleration index.

4. A method executed by an information processing apparatus, the method comprising:
   inputting voice data uttered by a subject;
   acquiring time-series data of sound pressure in the input voice data; and
   obtaining a Sound Pressure Change acceleration index that is an index based on a force toward a center and a force away from the center of the acquired time-series data of the sound pressure.

5. A non-transitory storage medium on which is stored a program for causing a computer to function as the inputter, the acquirer and the calculator of the information processing apparatus according to claim 1.

* * * * *